(12) United States Patent
Nezafat et al.

(10) Patent No.: US 7,375,520 B2
(45) Date of Patent: May 20, 2008

(54) METHOD FOR SPECTRALLY SELECTIVE B1 INSENSITIVE T2 PREPARATION CONTRAST ENHANCEMENT FOR HIGH FIELD MAGNETIC RESONANCE IMAGING

(75) Inventors: Reza Nezafat, Newton, MA (US); J. Andrew Derbyshire, Silver Springs, MD (US); Ronald Ouwerkerk, Baltimore, MD (US); Matthias Stuber, Ellicott City, MD (US); Elliot R. McVeigh, Phoenix, MD (US)

(73) Assignees: The United States of America as represented by the Department of Health, Washington, DC (US); Johns Hopkins University, Baltimore, MD (US)

( * ) Notice: Subject to any disclaimer, the term of this patent is extended or adjusted under 35 U.S.C. 154(b) by 7 days.

(21) Appl. No.: 11/409,511

(22) Filed: Apr. 20, 2006

(65) Prior Publication Data

US 2006/0284615 A1 Dec. 21, 2006

Related U.S. Application Data

(63) Continuation of application No. 11/147,151, filed on Jun. 6, 2005.

(60) Provisional application No. 60/674,949, filed on Apr. 25, 2005.

(51) Int. Cl.
*G01V 3/00* (2006.01)
(52) U.S. Cl. ........................ 324/307; 324/312
(58) Field of Classification Search ................ 324/307, 324/312, 309, 306
See application file for complete search history.

(56) References Cited

U.S. PATENT DOCUMENTS

| 5,285,158 | A | | 2/1994 | Mistretta et al. |
| 5,417,214 | A | | 5/1995 | Roberts et al. |
| 6,094,049 | A | * | 7/2000 | Rosenfeld et al. .......... 324/307 |
| 6,674,282 | B2 | * | 1/2004 | Pines et al. ................. 324/307 |
| 2006/0253015 | A1 | * | 11/2006 | Nezafat et al. ............. 600/410 |

OTHER PUBLICATIONS

Nezafat et al., "B1-insensitive T2 preparation for improved coronary magnetic resonance angiography," Res. in Med. 55:858-865 (2006).
Brittain, et al., "Coronary Angiography with Magnetization-Prepared $T_2$ Contrast," Magnetic Resonance in Medicine, 33:689-696 (1995).
Norris, "Adiabatic Radiofrequency Pulse Forms in Biomedical Nuclear Magnetic Resonance," Concepts in Magnetic Resonance, 14:89-101 (2002).
Tannú, et al., "Adiabatic Pulses," NMR in Biomedicine, 10:423-434 (1997).
Garwood, et al., "The Return of the Frequency Sxeep: Designing Adiabatic Pulses for Contemporary NMR," Journal of MAgnetic Resonance, 153:155-177 (2001).

* cited by examiner

*Primary Examiner*—Louis M. Arana
(74) *Attorney, Agent, or Firm*—Klarquist Sparkman, LLP

(57) ABSTRACT

A $T_2$ preparation sequence uses a segmented BIR-4 adiabatic pulse with two substantially equal delays and is insensitive to $B_1$ field variations and can simultaneously suppress fat signals with low specific absorption rate (SAR). An adiabatic reverse half passage pulse is applied followed by a predetermined delay. An adiabatic full passage pulse is applied followed by a substantially equal delay, followed by an adiabatic half passage pulse. Fat signal suppression is achieved by increasing or decreasing either the first delay or the second delay.

23 Claims, 12 Drawing Sheets

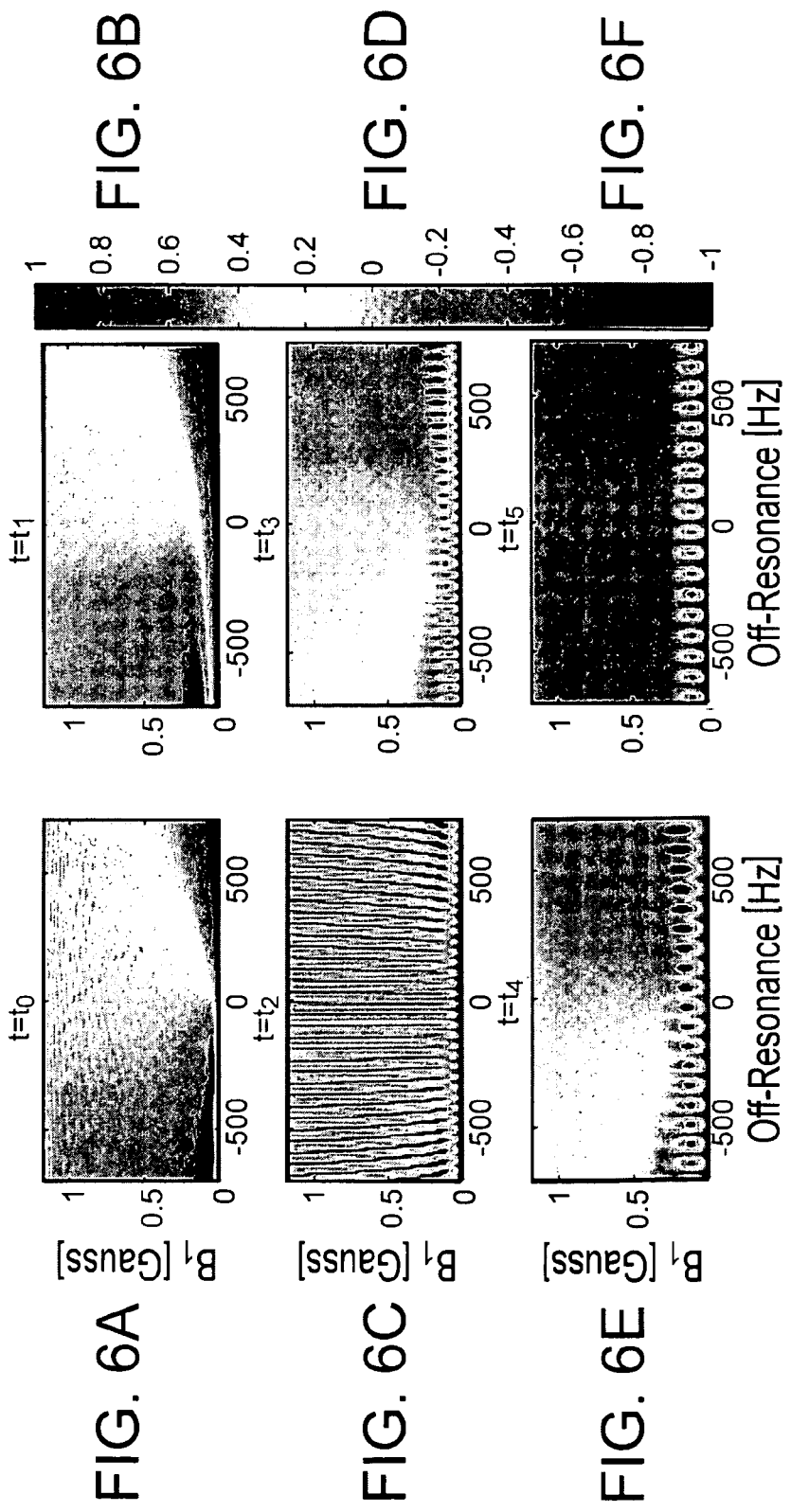

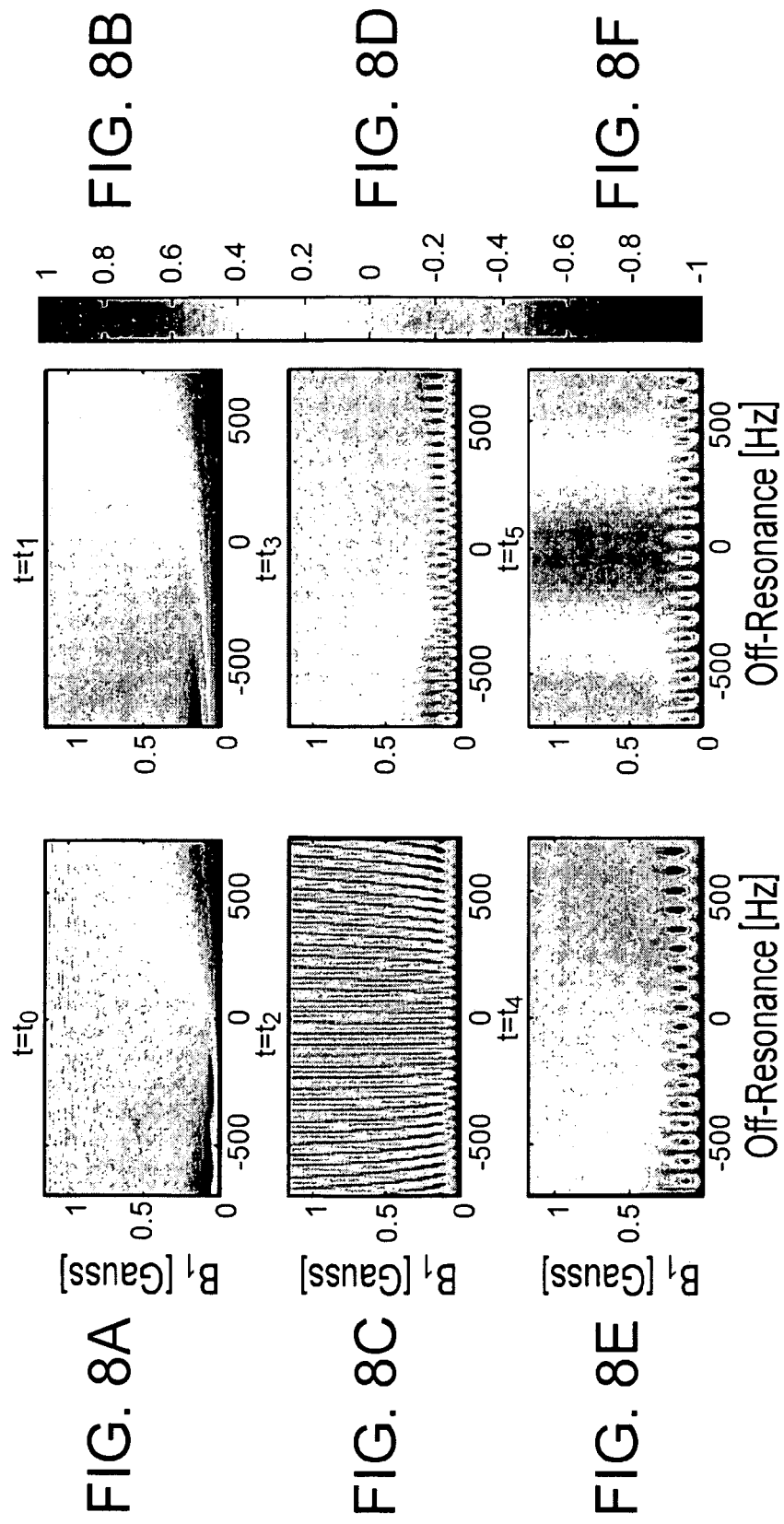

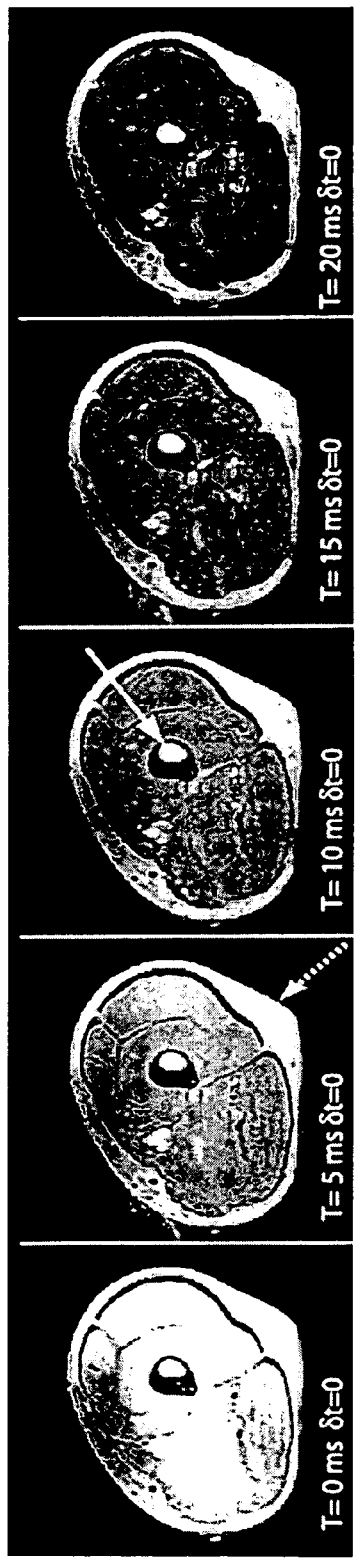
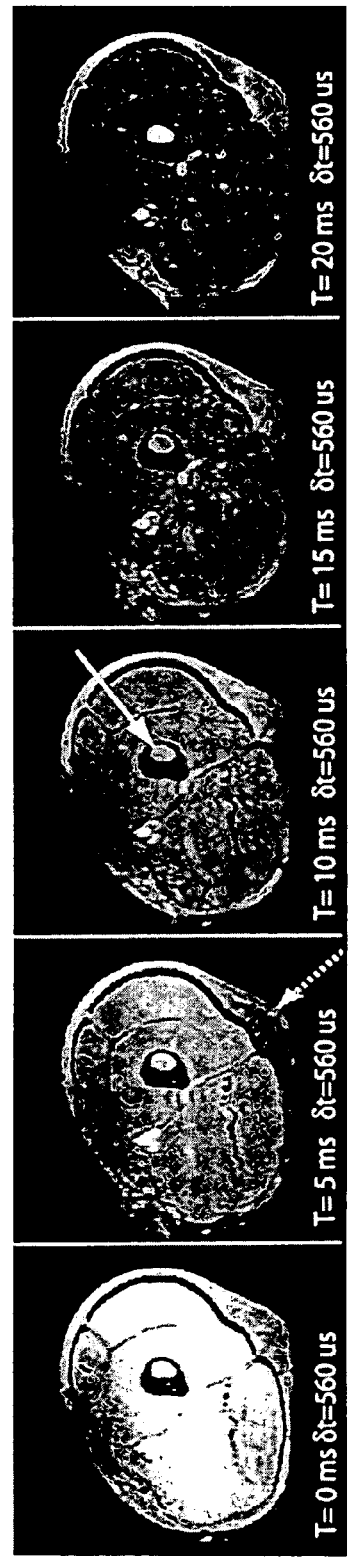
FIG. 13A  FIG. 13B  FIG. 13C  FIG. 13D  FIG. 13E
FIG. 13F  FIG. 13G  FIG. 13H  FIG. 13I  FIG. 13J ND FOR SPECTRALLY SELECTIVE
B1 INSENSITIVE T2 PREPARATION
CONTRAST ENHANCEMENT FOR HIGH
FIELD MAGNETIC RESONANCE IMAGING

CROSS REFERENCE TO RELATED APPLICATIONS

This application is a continuation-in-part of U.S. patent application Ser. No. 11/147,151, filed Jun. 6, 2005, which claims the benefit of U.S. Provisional Patent Application No. 60/674,949, filed Apr. 25, 2005, both of which are incorporated herein by reference.

FIELD

The disclosure pertains to magnetic resonance imaging.

BACKGROUND

Modern medical imaging methods permit physicians and researchers to more accurately diagnose, treat, and investigate a wide variety of disorders. Such imaging methods are based on various technologies including acoustic waves (ultrasound), radioactive decay (positron emission tomography), and nuclear magnetic resonance (magnetic resonance imaging). Each of these imaging techniques has its own characteristic advantages and disadvantages, but medical researchers, physicians and other practitioners continue to seek higher resolution, more reliable, less invasive, and more easily interpretable imaging systems and methods.

Magnetic resonance (MR) imaging systems generally use a static magnetic field ($B_0$) and a radio frequency magnetic field ($B_1$) to produce images. Unfortunately, the low signal-to-noise ratio (SNR) obtained with $B_0$ field strengths of about 1.5 T can limit the application of this technique. Application of higher magnetic fields (for example, 3 T) can improve SNR, but these higher magnetic fields are associated with undesirable changes in off-resonance susceptibilities, magnetic field inhomogeneities, and increased specific absorption rate (SAR). Because $B_0$ and $B_1$ cannot be controlled with arbitrary precision, especially at high field strengths, MR signals and images can be degraded by imperfections such as non-uniformities in these magnetic fields.

One important type of MR imaging is so-called $T_2$-weighted imaging in which image contrast is based primarily on spin-spin relaxation time constants (so-called "transverse relaxation") referred to as $T_2$. Conventional $T_2$ prep sequences used to prepare a specimen for extracting a $T_2$-weighted image consist of an initial 90° pulse to convert a substantial part of the longitudinal magnetization in the image field of view to transverse magnetization, followed by a combination of delays and RF pulses designed to refocus this transverse magnetization. Magnetization changes due to $T_2$ relaxation accumulate during these pulses and delays. A final 90° pulse is applied to return a substantial part of the refocused magnetization to the longitudinal axis. The $T_2$ relaxation between the application of the two 90° pulses provides the desired image contrast between sample components with different $T_2$ relaxation rates.

Some conventional $T_2$ preparation ($T_2$ prep) sequences have been designed to be robust to flow as well as to inhomogeneites in both $B_0$ and $B_1$. Such sequences use opposing pairs of so-called Malcom-Levitt (MLEV) pulses that can compensate pulse shape imperfections in the RF magnetic field $B_1$. Two representative sequences of such MLEV weighted composite $T_2$ prep sequences are shown in FIGS. 1A-1B. Pulses indicated as $180_x°$ are composite pulses, each consisting of a $90°_x 180°_y 90°_x$ pulse sequence. Such MLEV weighted composite pulses can compensate some imperfections in $B_1$, with larger numbers of such pulses providing increased compensation. However, increasing the number of MLEV pulses results in an increase in specific absorption rate (SAR), thus limiting the use of large numbers of MLEV pulses, especially at high $B_0$. Thus, MLEV pulse based $T_2$ prep is unsatisfactory in many applications.

Combinations of $T_2$ prep and spectrally selective fat suppression (FatSat) sequences are commonly used to enhance contrast in magnetic resonance images. In a typical $T_2$ prep sequence, the $T_2$ weighting is achieved by exciting the magnetization in the transverse plane with a 90 degree tip-down pulse, a train of equally-spaced composite 180 degree pulses with Malcom-Levitt (MLEV) phase cycling, and a 90° tip-up pulse. The most commonly used technique for suppression of the fat signal is based on excitation at the resonance frequency of the lipid protons. For most sequences, a narrow band RF pulse selectively excites the lipid magnetization into the transverse plane. This transverse magnetization is then dephased by a spoiling gradient to suppress the signal from fat in the acquisition sequences that follow the fat suppression sequence. However, conventional fat saturation methods are based on a chemically selective RF pulse which is typically relatively long (>10 ms at 1.5 T and >5 ms at 3 T). In some applications, such a pulse can be associated with significant increases in SAR and can require significant additional image acquisition time. In view of these and other disadvantages, improved imaging methods are needed to obtain the advantages of high field imaging with reduced sensitivity to imperfections in $B_0$ and $B_1$, reduced SAR, and fat saturation with reduced SAR.

SUMMARY

Methods and apparatus are described herein that offer reduced sensitivity to inhomogeneities in $B_1$ and $B_0$, particularly in $T_2$ prepared imaging in which image contributions from fat tissues are reduced by so-called "fat suppression." $T_2$ preparation sequences are provided that have spectral selectivity so that fat signal is suppressed without increasing total SAR. One example sequence is based on modifications of a BIR-4 pulse sequence.

In an example, magnetic resonance imaging methods comprise situating a sample in a longitudinal magnetic field to establish a longitudinal specimen magnetization. A reverse adiabatic half passage pulse is applied so as to produce a substantially transverse magnetization from the longitudinal magnetization, and the transverse magnetization is permitted to evolve for a first time interval. An adiabatic full passage pulse is then applied so as to substantially invert the transverse magnetization, and the inverted transverse magnetization is permitted to evolve for a second time interval. An adiabatic half passage pulse is applied so as to produce a $T_2$-weighted longitudinal magnetization from the evolved transverse magnetization. In some examples, a $T_2$-weighted image is obtained based on the $T_2$-weighted longitudinal magnetization. Such a pulse sequence is generally most insensitive to inhomogeneities in both $B_0$ and $B_1$ if the radiofrequency (RF) pulses are symmetrical in that a first portion of the adiabatic full passage pulse corresponds to the final adiabatic half passage pulse and the second portion of the adiabatic full passage pulse corresponds to the reverse adiabatic half passage pulse at the start of the sequence. In some examples, the first time interval and the second time interval are substantially the same. In other examples, the specimen includes spins of a first constituent and spins of a second constituent, and a difference between the first time interval and the second time interval is selected so that the adiabatic half passage pulse produces a longitudinal magnetization associated with primarily the first constituent. Typically, the difference between the first time interval and the second time interval is selected based on a difference between a Larmor frequency of the spins of the first constituent and the spins of a second constituent. In a representative example, the first constituent is water and the second constituent is fat.

The foregoing and other objects, features, and advantages of the invention will become more apparent from the following detailed description, which proceeds with reference to the accompanying figures.

BRIEF DESCRIPTION OF THE DRAWINGS

FIGS. 6A-6F illustrate normalized magnetization $M_z/M_{equilibrium}$ at various time points in the $T_2$-prep pulse sequence illustrated in FIGS. 7A-7B in the presence of $B_0$ resonance frequency offset (horizontal axis) and $B_1$ amplitude variation (vertical axis). As shown in FIG. 6F, $B_1$ magnitudes of at least about 0.20 Gauss produce substantially the same normalized magnetization.

FIGS. 8A-8F illustrate normalized magnetizations $M_z/M_{equilibrium}$ at various time points in the $T_2$-prep pulse sequence with fat suppression illustrated in FIGS. 9A-9B in the presence of $B_0$ resonance frequency offset (horizontal axis) and $B_1$ amplitude variation (vertical axis).

FIGS. 13A-13E are representative transverse images of a human thigh obtained with adiabatic $T_2$ prep and symmetric delays ranging up to 20 ms.

FIGS. 13F-13J are representative thigh images corresponding to those of FIGS. 15F-15E with an additional fat sat delay of 560 µs.

DETAILED DESCRIPTION

Figure 1B:
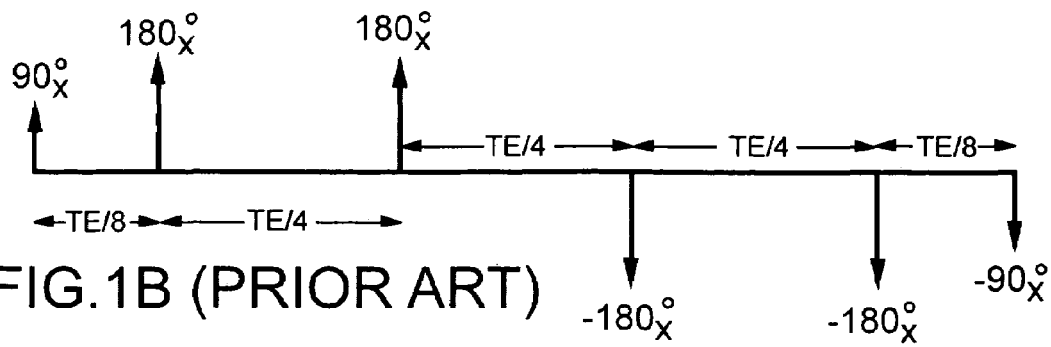
FIGS. 1A-1B illustrate standard Malcom-Levitt (MLEV) weighted $T_2$ preparation sequences.
Figure 1A:
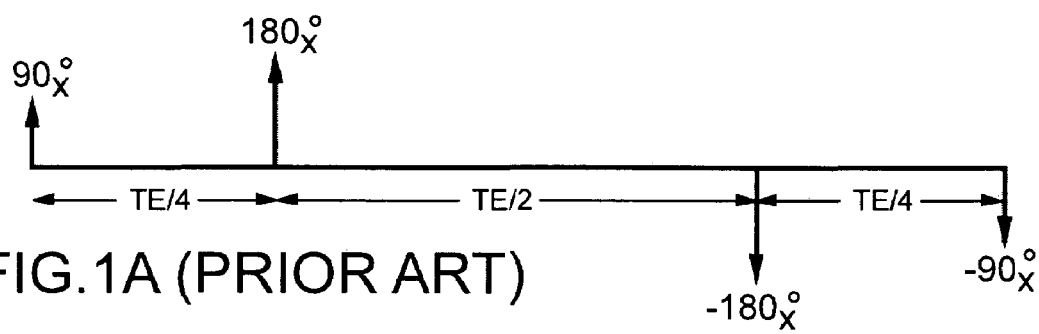

As used in this application and in the claims, the singular forms "a," "an," and "the" include the plural forms unless the context clearly dictates otherwise. Additionally, the term "includes" means "comprises." Disclosed below are representative embodiments of magnetic resonance apparatus that can be configured to produce representative pulse sequences associated with adiabatic $T_2$ preparation. While particular examples and applications for the disclosed embodiments are also disclosed, the described systems, methods, and apparatus should not be construed as limiting in any way. Instead, the present disclosure is directed toward all novel and nonobvious features, aspects, and equivalents of the various disclosed embodiments, alone and in various combinations and sub-combinations with one another. The disclosed systems, methods, and apparatus are not limited to any specific aspect, feature, or combination thereof, nor do the disclosed systems, methods, and apparatus require that any one or more specific advantages be present or problems be solved. In addition, the attached figures may not show the various ways in which the disclosed systems, methods, and apparatus can be used in conjunction with other systems, methods, and apparatus, and components that are well known in the art are not described in detail.

Examples of the disclosed technology include magnetic resonance (MR) methods, systems, and apparatus configured to apply adiabatic pulses to a specimen. Such pulses can be described as electrical pulses such as radio-frequency (RF) pulses configured to produce an associated RF magnetic field that is applied to the specimen. As used herein, an adiabatic RF pulse is a pulse that includes an amplitude modulation and a frequency (or phase) modulation configured to produce a common nutation of substantially all water proton spins in a specimen (or spins of some other species). The adiabatic properties of an RF pulse are determined by the time dependent functions describing the off-resonance frequency, the difference between the RF frequency and the Larmor frequency of the spins, and the local $B_1$ field strengths. Specifically the rate of change in the ratio of the local $B_1$ field strength and the off-resonance frequency determines the adiabaticity of the pulse. Where the adiabatic conditions are met, above a threshold $B_1$ field strength, the adiabatic pulse can achieve a desired nutation with large $B_1$ field variations of a factor 10 times or more above this threshold field strength. The common nutation produced with such pulses can be achieved throughout a specimen volume even in the presence of non-uniformities in a magnitude of an effective RF magnetic field $|B_{eff}|$ or the static longitudinal magnetic field $B_0$. For example, the common nutation can be obtained with magnetic field variations of up to 10%, 20%, 50%, or more. Adiabatic pulses can be associated with common nutations of about 90°, about 180°, or other angles. Adiabatic pulses associated with rotations of about 180° are referred to as adiabatic full passage (AFP) pulses. Adiabatic pulses associated with rotations of about 90° are referred to as adiabatic half passage (AHP) pulses. Reverse" and "forward" pulses are associated with frequency or phase modulations that are approximately inverses. Typically, an AFP pulse can be defined as a combination of a forward AHP and a reverse AHP (rAHP).

While typical adiabatic pulses include amplitude and frequency modulations that produce the common nutation for substantially all spins of a selected species, in some examples the modulations are selected to produce the common nutation only for spins within a selected spin bandwidth, the extent of which is inversely proportional to the pulse duration. Pulses having a finite bandwidth can also be referred to as frequency selective adiabatic pulses.

Figure 2:
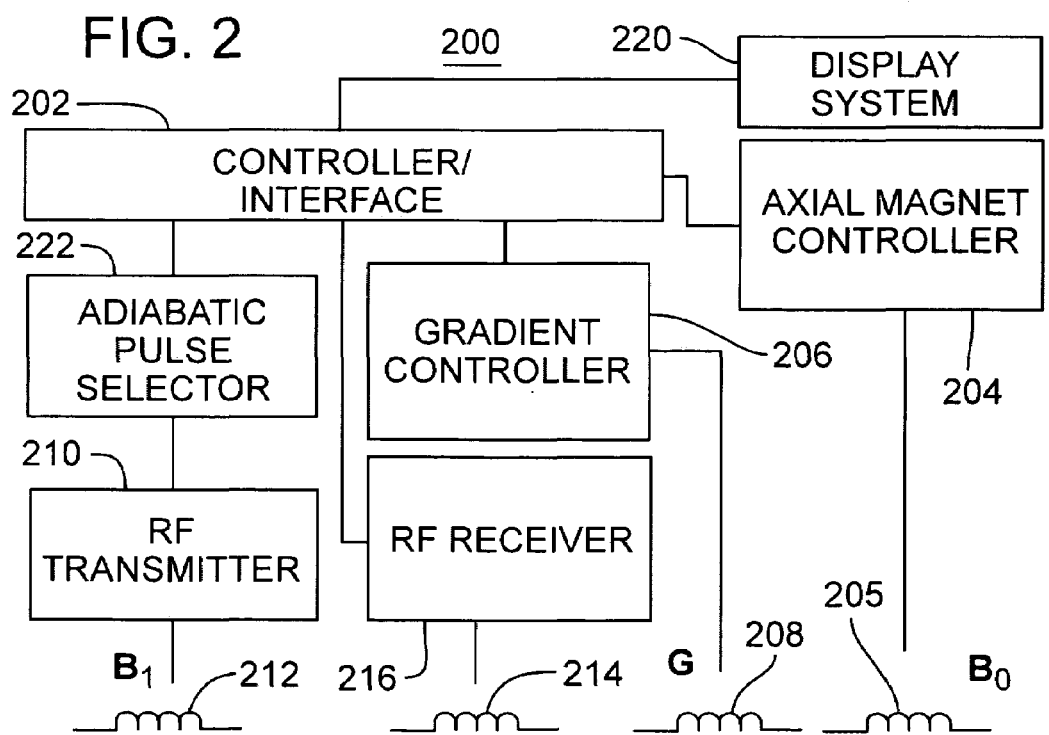
FIG. 2 is a schematic diagram of a magnetic resonance imaging system configured to select and apply adiabatic pulses in adiabatic $T_2$ preparation sequences.

A representative magnetic resonance imaging (MRI) apparatus 200 is illustrated in FIG. 2. The MRI system 200 includes a controller 202 that is typically programmed by a clinician with a series of commands corresponding to a particular imaging sequence. The command sequences can be entered with a keyboard, or a pointing device such as a mouse, or other input device. Command sequences can be stored by the controller 202 for retrieval from a hard disk, floppy disk, or other computer readable media, and can be selected from a menu, so that a clinician can easily select among an imaging protocol from various command sequences. Alternatively, command sequences or other operational information can be remotely stored and retrieved via a network connection from remote storage from, for example, a remote server.

As used herein, the magnetic field $B_0$ is directed along a +z-axis in a xyz coordinate system. A plane parallel to an xy-plane (perpendicular to the z-axis) is referred to as a transverse plane. The MRI apparatus 200 includes a magnet controller 204 that controls the spatial homogeneity of the magnetic field $B_0$ with one or more field coils 205, creating linear, quadratic, and higher order variations of the magnetic field in the x, y, or z directions. For example, field variations can include terms that are functions of, for example, $x^2$, $y^2$, $z^2$, xy, yz, xz, $x^2y$, $y^2z$, $xz^2$. A gradient controller 206 activates a gradient coil 208 to produce a magnetic field gradient G that is typically applied as a pulse. The gradient coil 208 can consist of one or more coils or subcoils that are configured to apply particular components (such as x, y, or z-components) of the gradient field G.

A radio-frequency (RF) transmitter 210 is configured to generate RF pulses that are applied to a transmitter coil 212 to produce the RF magnetic field $B_1$. A receiver coil 214 detects changes in magnetization in the specimen and communicates the detected magnetization changes to an RF receiver 216. The RF receiver 216 processes the detected magnetization changes and provides corresponding electrical signals or image data to the controller 202 based on these changes. The particular arrangement of FIG. 2 is selected for convenience, and components of such an MRI apparatus can be arranged in other ways.

A specimen to be imaged is exposed to the axial magnetic field $B_0$, one or more field gradients G, and one or more radiofrequency fields $B_1$ that are selected by the controller 202. Changes in specimen magnetization are detected by the receiver coil 214 and processed by the RF receiver 216. The RF pulse is typically represented as product of a pulse envelope $B_1$ and a complex exponential $\exp(i\omega_{RF}t)$, wherein t is time, i is the square root of $-1$, and $\omega_{RF}$ is an excitation carrier frequency. The excitation frequency $\omega_{RF}$ is generally selected to be approximately equal to a resonance frequency of one or more constituents of the specimen. The resonance frequency $\omega_0$ is proportional to a product of a gyromagnetic ratio $\gamma$ (a material constant) and a magnitude of the axial field $B_0$. Adiabatic RF pulses generally provide both amplitude and frequency modulation, so that the pulse envelope $B_1$ and the excitation carrier frequency $\omega_{RF}$ are time varying. For convenient implementation in some MRI systems, a pulse frequency modulation can be defined based on an associated phase modulation.

The field gradient G exposes the specimen to a non-uniform magnetic field, so that slices of the specimen can be selected for imaging. Slice selection is commonly performed by applying a gradient so that the local resonant frequency is a linear function of the spatial position offset in the slice direction. Application of a band-limited RF pulse then selectively excites only those spins within a positional range such that their frequency lies in bandwidth of the RF pulse. Detecting changes in magnetization slice by slice permits image formation.

With only the axial magnetic field $B_0$ applied, some magnetic dipoles of sample constituents align with the axial magnetic field $B_0$ to produce an equilibrium magnetization $M_0$ that generally has only a +z-directed component. The specimen includes individual magnetic dipoles of dipole moment $\mu$ that precess about the direction of $B_0$ (the z-axis) at the frequency $\omega_0 = \gamma B_0$ that is also referred to as the Larmor frequency, wherein $B_0$ is the magnitude of the field $B_0$. Changes in magnetization are generally described with reference to an xyz coordinate system that rotates about the axial direction at the Larmor frequency. The z-axis of such a rotating coordinate system is the same as the z-axis of a stationary coordinate system while the x-axis and y-axis of the rotating coordinate system rotate in a transverse plane.

Application of a selected RF pulse can rotate a magnetization or one or more components thereof. An RF pulse of duration and magnitude at spin resonance frequency having a magnitude and duration sufficient to produce a 180 degree rotation is referred to as a 180° pulse and an RF pulse sufficient to produce a 90 degree rotation is referred to as a 90° pulse. The axis of rotation of such pulses can be selected based on the direction in which the corresponding pulse magnetic field is applied. Such RF pulses are generally referred to as "hard" pulses. Adiabatic pulses can also be applied, and are described below.

An adiabatic pulse selector 222 is configured to select adiabatic RF pulses for application with the RF transmitter 210 and the RF coil 212 as directed by the controller 202. The adiabatic pulse selector 222 is shown in FIG. 2 as a separate component, but can be included as part of the controller 202, the RF transmitter 210, or provided as a combination of these or other portions of the MRI apparatus. The adiabatic pulse selector 222 generally defines so-called "adiabatic" RF pulses in which both RF pulse amplitude and frequency (or phase) are time varying. Such pulses are configured to exhibit reduce sensitivity to inhomogeneities in $B_0$ and $B_1$. Adiabatic pulses can be selected so that magnetization vector components parallel and anti-parallel to an effective RF magnetic field $B_{eff}$ field remain substantially parallel and anti-parallel, respectively, while magnetization vector components perpendicular to the effective RF magnetic field $B_{eff}$ precess and remain substantially perpendicular to the effective RF magnetic field $B_{eff}$. Adiabatic pulses produce effective RF magnetic fields whose orientation changes more slowly than a rotation of sample magnetization about the effective RF magnetic field. Generally, the effective radiofrequency magnetic field $B_{eff}$ can be represented as a sum of the applied RF magnetic field ($B_1$) and $$\frac{\Delta \omega}{\gamma} \hat{z},$$

wherein $\Delta \omega = \omega - \omega_0$, $\omega$ is an angular frequency of the applied RF magnetic field $B_1$, $\omega_0$ is a spin resonance (Larmor) frequency, $\gamma$ is a gyromagnetic ratio, and $\hat{z}$ is a unit vector parallel to the longitudinal axis. In conventional "hard" RF pulses, $\Delta \omega = 0$, and the effective RF magnetic field is the same as the applied RF magnetic field $B_1$. Examples of such adiabatic pulses include so-called adiabatic fast passage (AFP) and adiabatic half-passage (AHP) RF pulses. Using adiabatic refocusing pulses, a transverse magnetization can be refocused in the presence of substantial $B_1$ field inhomogeneities.

The adiabatic pulse selector 222 can select from among many adiabatic modulation functions in order to define adiabatic pulses. For example, some functions that can be used to define amplitude/frequency modulation portions of adiabatic pulses include sin/cos, tan/sec, tanh/sech, as well as numerically defined modulations such as numerically optimized modulations (NOMs). One representative AFP pulse can be defined based on a hyperbolic secant and hyperbolic tangent function pair, wherein $$B_1(t) = B_{1max} \text{sech}(\beta(2t/T - 1))$$

$$\Delta \omega(t) = \Delta \omega_{max} \tanh(\beta(1 - 2t/T)),$$

wherein $\beta$ is a dimensionless truncation factor, typically assigned a value of about $\text{sech}^{-1}(0.01)$, t is time, T is a total pulse duration, and $B_{1max}$ and $\Delta \omega_{max}$ are a maximum amplitude and frequency modulation, respectively. Pulse parameters such as $B_{1max}$ and $\Delta \omega_{max}$ can be selected based on pulse width, bandwidth, SAR deposition, RF amplifier constraints, and adiabaticity conditions. The adiabatic pulse selector 222 can include a library of adiabatic pulse definitions and/or include a processor configured to specify adiabatic pulse properties based on stored parameters, or on computed parameters.

Various adiabatic pulses can be used instead of the hyperbolic secant pulse described above. Selection of a particular pulse can be made based on application requirements. In contrast to conventional "hard" RF pulses lacking substantial frequency or phase modulation, adiabatic pulses are generally configured so that a magnetization follows the applied time-varying adiabatic RF magnetic field direction. Adiabatic pulses can refocus transverse magnetization in the presence of non-uniform $B_0$ and $B_1$. So-called $B_1$ insensitive rotation (BIR) pulses can be used that are composites of two or more pulses. For example, a BIR-3 pulse includes a first pulse segment that produces an adiabatic inversion, and a second pulse segment that compensates phase dispersion produced by the first pulse segment. This pulse produces dephasing due to off-resonance excitation, and is not generally suitable for slice selection. Other BIR pulses can have similar disadvantages. A lower power adiabatic refocusing method is based on applying substantially similar (or identical) adiabatic fast passage pulses in which a second adiabatic fast passage pulse substantially compensates phase variations generated by the first adiabatic fast passage pulse. Some functions that can be used to define adiabatic pulses include a Lorenz function, a Gaussian function, or a Hanning function.

A frequency or phase modulated RF pulse that functions according to the adiabatic principle can be used as an accurate saturation or inversion pulse in the presence of enhanced magnetic field inhomogeneity. A composite adiabatic pulse can be constructed by combining multiple adiabatic half (AHP) or full passage (AFP) pulses. Reverse adiabatic half passage pulses (rAHP) which are substantially time mirrors of adiabatic half passage pulses can be used in composite pulses. An AFP produces a rotation of about 180° and an AHP produces a rotation of about 90°.

A so-called $B_1$-insensitive rotation (BIR-4) pulse is a composite adiabatic pulse which consists of three segments, (i) a rAHP, (ii) an AFP and (iii) an AHP. In this pulse, a desired flip angle $\Delta_\theta$ is achieved by introducing a phase step of $\Delta_{\theta/2}$ for the duration of the middle AFP segment. The 0-degree BIR-4 pulse with a symmetric long delay before and after the middle segment can be used as a zero or double quantum filter as described in de Graaf et al., "Spectral editing with adiabatic pulses." J. Magn. Reson., B109:184-193 (1995). In addition, a single delay between segments 1 and 2 of a BIR-4 pulse can be used for solvent suppression.

Figure 3A:
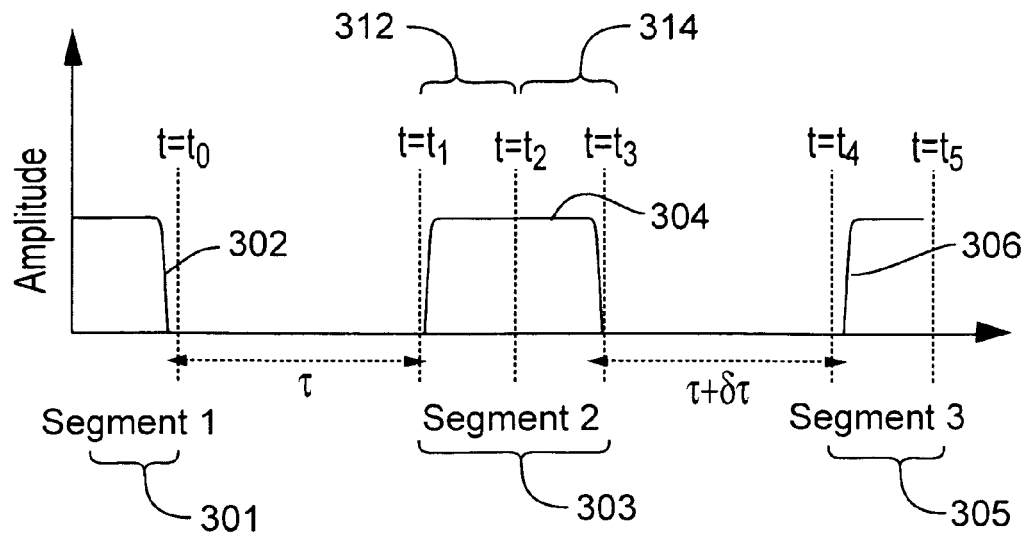
FIGS. 3A-3B illustrate amplitude and frequency (phase) contributions, respectively, of a spectrally selective, $B_1$ insensitive, $T_2$-preparation pulse sequence.
Figure 3B:
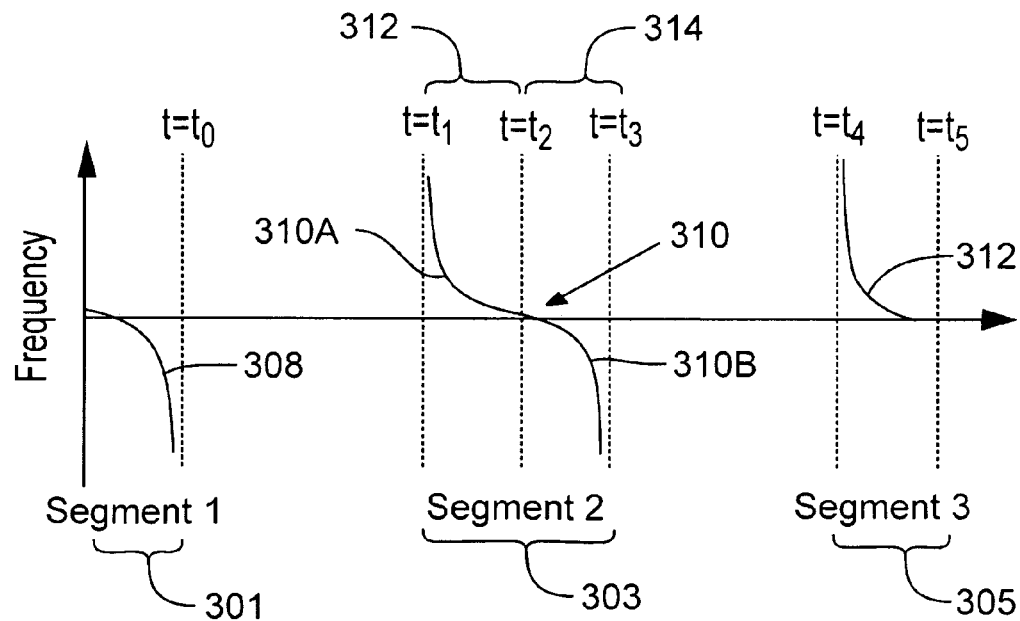
Figure 4A:
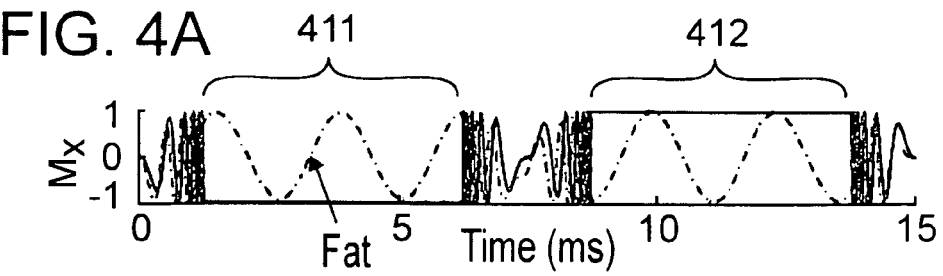
FIGS. 4A-4C illustrates trajectories of the magnetization vector $M=[M_x, M_y, M_z]$ during the pulse sequence illustrated in FIGS. 4D-4E. The magnetization vector for water is shown as a solid line and the magnetization vector for fat is shown as a dashed line. The magnetization vector in both water and fat returns to the longitudinal axis at the end of the sequence. Relaxation effects are neglected.
Figure 4B:
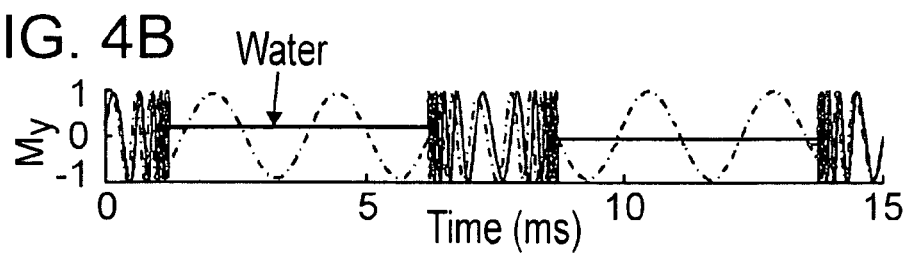
Figure 4C:
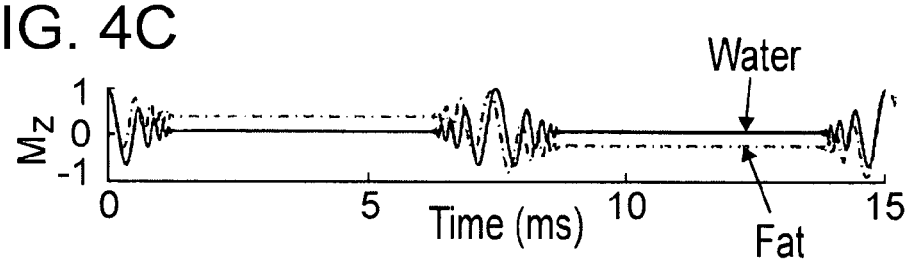
Figure 4D:
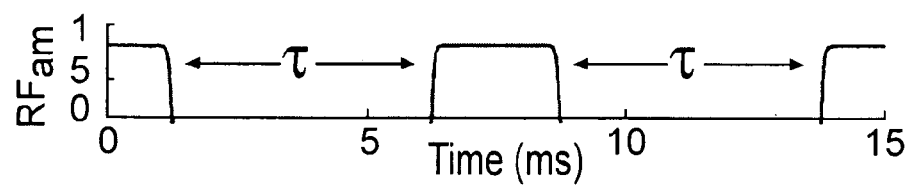
FIGS. 4D-4E illustrate amplitude and frequency (phase) modulations, respectively, of a spectrally selective, $B_1$ insensitive, $T_2$-preparation pulse sequence used to produce the time varying magnetization components $M_x$, $M_y$, and $M_z$ illustrated in FIGS. 4A-4C. The magnetization vector for water is shown as a solid line and the magnetization vector for fat is shown as a dashed line. Both of these magnetization vectors return to the longitudinal axis at the end of the sequence, diminished only by $T_2$ decay.
Figure 4E:
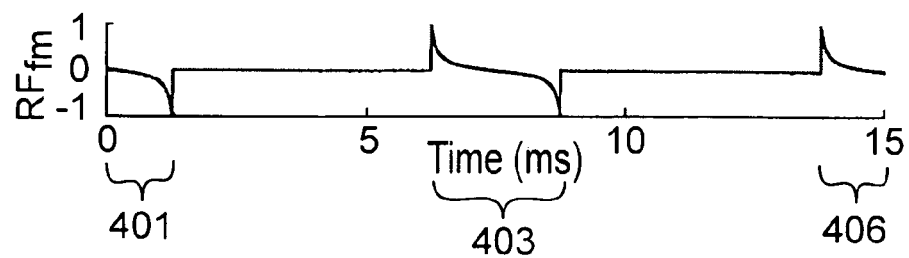

FIGS. 3A-3B include a schematic representation of an example $T_2$ prep sequence. A first pulse segment 301 is defined by an amplitude specification 302 and a frequency (phase) specification 308. The first pulse segment 301 can be referred to as a so-called reverse adiabatic half passage pulse or "rAHP." The rAHP pulse excites a longitudinal magnetization $B_0$ into a transverse plane. Application of the first pulse segment 301 is followed by a delay time of τ during which the magnetization precesses and relaxes based on its intrinsic relaxation times $T_1$, $T_2$. A second pulse segment 303 having an amplitude specification 304 and a frequency (phase) specification 310 is then applied. The second pulse segment 303 includes a first portion 312 and a second portion 314, and the frequency specification includes respective first portions 310A, 310B. The second pulse segment 303 is substantially an adiabatic full passage (AFP) pulse with a modulation function corresponding to, in part, that of the rAHP pulse of the first pulse segment 301. During the second pulse segment 303, magnetization vectors initially perpendicular to the effective applied RF field $B_1$ remain in a plane perpendicular to $B_1$ and acquire an additional phase contribution. Magnetization vectors parallel to the effective field $B_1$ are substantially inverted. During a second delay of duration τ+δτ, the magnetization continues to precess and relax. In some cases δτ=0, and the same delay is used between pulse segments 301, 303 and 303, 305. Such a pulse sequence is referred to as having a symmetric delay.

A third pulse segment 303 that is substantially an AHP is applied to return the magnetization to the longitudinal axis. The acquired phase produced by the first pulse segment 301 (the rAHP pulse), the first delay of duration τ, and a first portion 312 of the second pulse segment 303 is substantially compensated by phase contributions acquired from a second portion 314 of the second pulse segment 303, the third pulse segment, and second delay τ. The additional delay δτ can be selected for fat saturation as described below.

Although the single AFP pulse does not generally result in the refocusing of the magnetization from the first excitation, the use of a symmetric sequence of the pulses, at least partially compensates for the phase acquired in the AFP pulse, i.e., all isochromats experience the adiabatic condition being returned to longitudinal orientation. The long delay between segments can be set to achieve a desired contrast between different tissues based on the intrinsic $T_2$ value of the tissues. Longer delay results in more sensitivity to $T_2$ decay but SNR will decrease due to $T_2$ and $T_1$ relaxation.

As shown in FIG. 3B, the frequency modulation 308 of the first segment 301 and the frequency modulation 312 of the third segment 305 can be combined to produce the frequency modulation 310 of the second segment. A first portion 314 of the frequency modulation 310 corresponds to the frequency modulation 312; a second portion 316 of the frequency modulation 310 corresponds to the frequency modulation 308. A typical $B_1$ insensitive pulse sequence includes a frequency modulation having a first portion and a second portion. These frequency modulation portions are applied as follows. In the first pulse segment, the first portion is applied. In the second pulse segment, a second portion is applied followed by the first portion. In the third pulse segment, the second portion is applied.

Referring to FIG. 3B, a frequency modulation 308 in the first pulse segment 301 is substantially the same as a frequency modulation 310B applied in the second portion 314 of the second pulse segment 303. The frequency modulation 312 of the third pulse segment 305 is substantially the same as a frequency modulation 310A applied in the first portion of the second pulse segment 303. In addition, the frequency modulations 308, 310A and 312, 310B are substantially inverses. For example, if the frequency modulation 308 applied in the first pulse segment 301 is expressed as $FM_{308}=f(t)$, wherein $f(t)$ is a function of time t, then the frequency modulation 310A applied in the second pulse segment 303 corresponds to $FM_{310}=-f(-t)$. With such frequency modulation, the first, second, and third pulse segments can be referred to as "matched."

There are numerous choices for the amplitude and frequency modulations of the adiabatic BIR-4 pulse segments. A hyperbolic tangent function and a tangent function can be conveniently used so that the amplitude modulation of the $T_2$-prep sequence is given by:

$$A(t) = \begin{cases} B_{max}\tanh\left[\gamma\left(1 - \frac{4t}{T}\right)\right] & 0 \leq t < T/4 \\ 0 & T/4 \leq t < T/4 + \tau \\ B_{max}\tanh\left[\gamma\left(4\frac{t-\tau}{T} - 1\right)\right] & T/4 + \tau \leq t < T/2 + \tau \\ B_{max}\tanh\left[\gamma\left(3 - 4\frac{t-\tau}{T}\right)\right] & T/2 + \tau \leq t < 3T/4 + \tau \\ 0 & 3T/4 + T \leq t < 3T/4 + 2\tau \\ B_{max}\tanh\left[\gamma\left(4\frac{t-2\tau}{T} - 3\right)\right] & 3T/4 + 2\tau \leq t < T + 2\tau \end{cases}$$

and the frequency modulation by:

$$\omega_{rf}(t) = \begin{cases} -\dfrac{\tan\left(4\beta\frac{t}{T}\right)}{\tan\beta} & 0 \leq t < T/4 \\ 0 & T/4 \leq t < T/4 + \tau \\ -\dfrac{\tan\left(\beta\left(4\frac{t-\tau}{T} - 2\right)\right)}{\tan\beta} & T/4 + \tau \leq t < T/2 + \tau \\ -\dfrac{\tan\left(\beta\left(4\frac{t-\tau}{T} - 2\right)\right)}{\tan\beta} & T/2 + \tau \leq t < 3T/4 + \tau \\ 0 & 3T/4 + \tau \leq t < 3T/4 + T) \\ -\dfrac{\tan\left(\beta\left(4\frac{t-2\tau}{T} - 4\right)\right)}{\tan\beta} & 3T/4 + 2\tau \leq t < T + 2\tau \end{cases},$$

wherein β and γ are dimensionless constants that based on the adiabatic condition, t is time, T is the total duration of all three segments of the RF pulse sequence (about four times the duration of the adiabatic half passage pulse), and τ is an insertion delay. The above equations are based on symmetrical decay, but can be modified for nonzero values of δτ. $B_{max}$ is a maximum amplitude of the modulation function (frequency sweep) and is determined by the power necessary to substantially satisfy the adiabatic condition. The frequency modulation can also be replaced by an equivalent phase modulation. The phase difference between the second pulse segment 303 and the first pulse segment 301 and the third pulse segment 305 can be any integer multiple of 180° yielding a flip angle α=0°.

As shown in FIGS. 3A-3B, the pulse segments 301, 303 have a first relative delay τ and the pulse segments 303, 305 have a second relative delay τ+δτ. During these delays, the transverse magnetization undergoes free precession, and acquires a phase that depends on spin resonant frequency. If the additional delay δτ=0 (i.e., the second delay is τ), the first and second delays are substantially equal so a phase acquired in the first delay by magnetization with a resonance frequency offset of Δω is substantially compensated by a corresponding but opposite phase accumulated during the second delay. However, if the first and second delays are not equal (i.e., $\delta\tau \neq 0$), acquired phase in the first delay due to resonant frequency offsets is only partially compensated by the second delay, resulting in a residual phase $\phi$. This residual phase is determined by the frequency offset $\Delta\omega$ and difference between the first and second delays $\delta\tau$. This phase difference can be used to select specimen constituents for enhancement or suppression in imaging. For example, a phase difference between the fat and water signal components can be set to 90° by selecting the delay different $\delta\tau = \frac{1}{4}\Delta f$, wherein $\Delta f$ is a resonant frequency offset between fat and water. For a chemical shift between fat and water of 440 Hz at 3 T, a $\delta\tau = 560$ μs produces a 90° phase difference. The delay T and the delay difference $\delta\tau$ can be selected to that magnetization associated with the water component is substantially returned to the longitudinal axis by the third pulse segment 305 (an AHP pulse segment) of the pulse sequence. However, this AHP pulse will not return the fat signal component to the longitudinal axis because of the 90° phase shift, and instead, magnetization components associated with fat remain in the transverse plane. This transverse magnetization can be dephased by a spoiling gradient, resulting in suppression of the fat signal without disturbing the signal associated with magnetization of the water component. In contrast to conventional fat saturation schemes, this method has only a small increase in sequence duration (about 600 μs).

Pulse sequences without and with an additional (asymmetric) delay are illustrated in FIGS. 4D-4E and FIGS. 5D-5E, respectively. The associated magnetization components for both a water and a fat portion of a specimen are graphed in FIGS. 4A-4C and FIGS. 5A-5C, respectively, with respect to a frame of reference rotating with the water component magnetization. Referring to FIGS. 4A-4E, a first pulse segment 401 (an rAHP pulse) is applied to a specimen having a water component and a fat component. The magnetization of both water and fat components is initially substantially longitudinal (along a direction of the magnetic field $B_0$, a z-direction as used herein) and the rAHP pulse rotates the water magnetization from the z-axis to be along a −y axis (with a small portion along a +y-axis). The rotated water magnetization is constant in the rotating frame of reference after the rAHP pulse during a first interval 411, ignoring $T_1$ and $T_2$ effects. However, the magnetization of the fat component is not totally tipped into transverse plane, and has components along all three coordinate axes. During the first delay, the fat signal will precess with the resonance offset of the fat (420 Hz at 3 T). Thus, although the magnetization of the fat component is largely rotated into the transverse plane (the xy-plane) by the pulse segment 401, this magnetization oscillates at the offset frequency during the first delay 411. A pulse segment 403 (an AFP segment) reverses the both the water and fat phases so that the x, y, and z-components of the water and fat magnetizations are inverted. The water magnetization remains substantially constant during a second interval 412 (ignoring $T_1$ and $T_2$ effects) while the fat magnetization oscillates due to the frequency offset between fat and water. A third pulse segment 405 rotates the water and fat magnetizations back to the z-axis. As a result, magnetizations for both water and fat are stored.

Figure 5A:
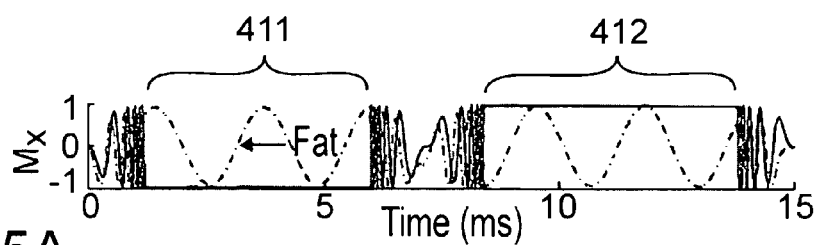
FIGS. 5A-5C illustrate trajectories of the magnetization vector $M=[M_x, M_y, M_z]$ during the pulse sequence illustrated in FIGS. 5D-5E. The magnetization vector for water is shown as a solid line and the magnetization vector for fat is shown as a dashed line. The magnetization vector for water (solid line) returns to the longitudinal axis at the end of the sequence, while the magnetization vector for fat (dashed line) remains in the transverse plane.
Figure 5B:
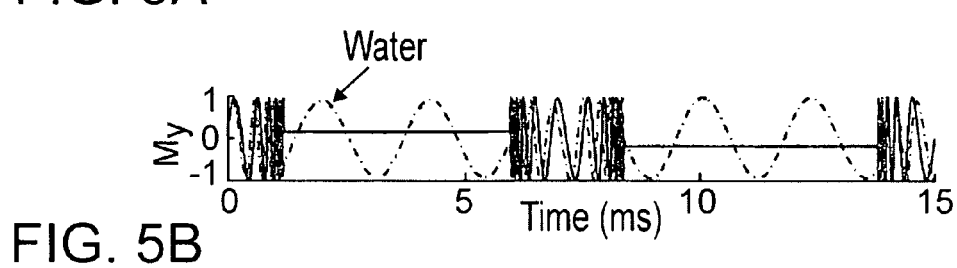
Figure 5C:
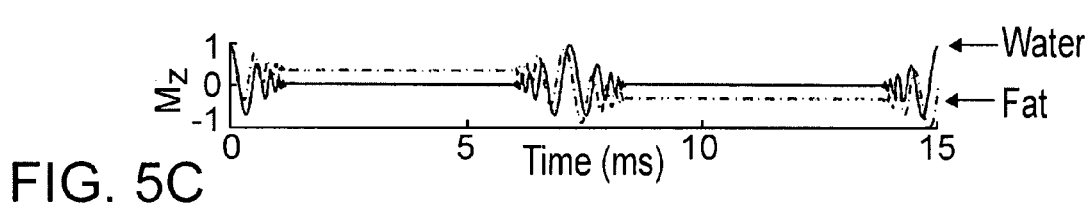
Figure 5D:
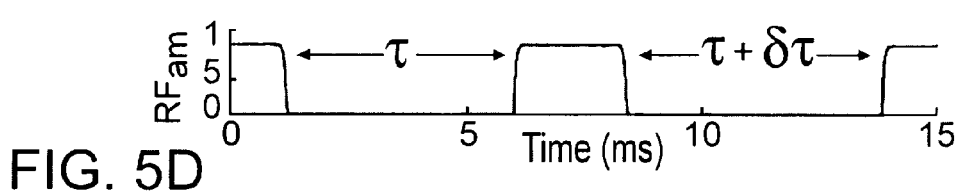
FIGS. 5D-5E illustrate amplitude and frequency (phase) modulations, respectively, of a spectrally selective, $B_1$ insensitive, $T_2$-preparation pulse sequence used to produce the time varying magnetizations illustrated in FIGS. 5A-5C. A final pulse segment is delayed relative to the final pulse segment of FIGS. 4D-4E so that the magnetization vector for fat is substantially in the transverse plane for dephasing with a spoiling gradient.
Figure 5E:
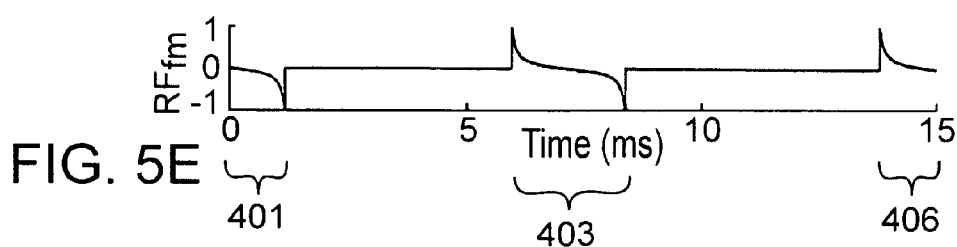
Figure 7A:
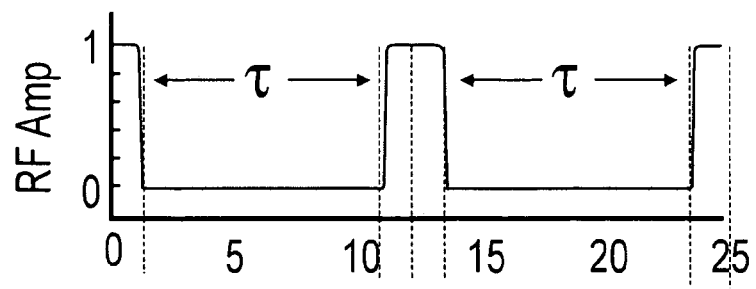
FIGS. 7A-7B illustrate amplitude and frequency (phase) contributions, respectively, of a spectrally selective, $B_1$ insensitive, $T_2$-preparation pulse sequence used to calculate the normalized magnetizations of FIGS. 6A-6F. The resonance frequency of fat is about 440 Hz at 3 T. In this simulation, $T_1$=1115 ms and $T_2$=55 ms, and the delay $\tau$=20 ms. A tanh modulation function with duration of 1.25 ms for each pulse segment was used.
Figure 7B:
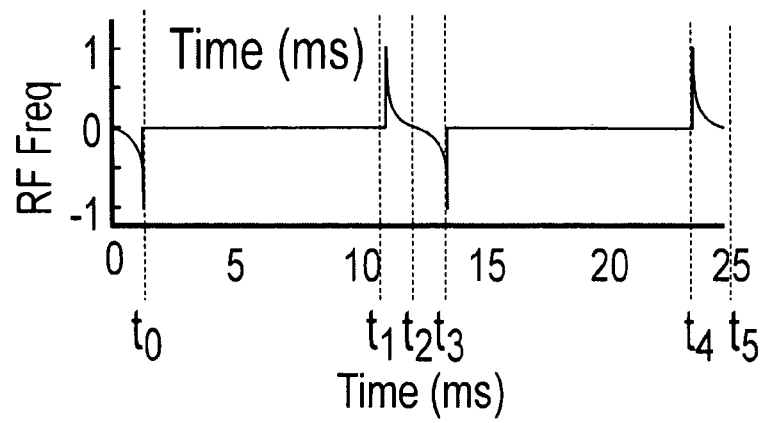
Figure 9A:
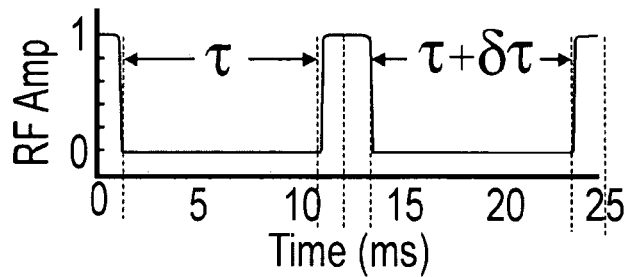
FIGS. 9A-9B illustrate amplitude and frequency (phase) contributions, respectively, of a spectrally selective, $B_1$ insensitive, $T_2$-preparation pulse sequence used to calculate the normalized magnetizations of FIGS. 8A-8F. The resonance frequency of fat is about 440 Hz at 3 T. In this simulation, T1=1115 ms and T2=55 ms, and the delay T=20 ms. A tan h modulation function with duration of 1.25 ms for each pulse segment was used. The additional delay was $\delta\tau$=560 µs for fat saturation.
Figure 9B:
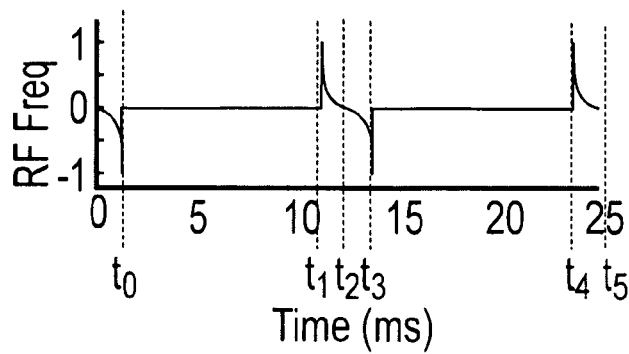
Figures 10A, 10B, 10C, 10D, 10E:
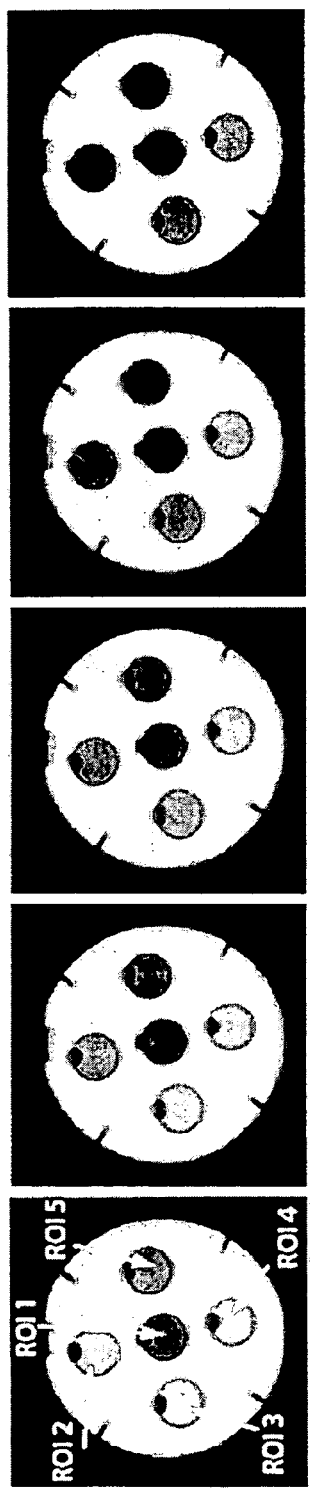
FIGS. 10A-10E are images of a doped-water phantom containing 5 tubes with different $T_2$ values using a $T_2$-prep sequence such as that shown in FIGS. 3A-3B with delays of $\tau$=0 ms, 5 ms, 10 ms, 15 ms, and 20 ms, respectively. Enhanced contrast is visible in different tubes.

Fat magnetization can be suppressed as illustrated in FIG. 5A-5D. The pulse sequence illustrated in FIGS. 5D-5E differs from that of FIGS. 4D-4E only in that a second delay 512 is greater than the first delay 411 by $\delta\tau = \frac{1}{4}\Delta f$. Referring to FIGS. 5A-5C, the fat and water magnetizations evolve as in FIGS. 4A-4C in response to the pulse segments 401, 403, and the first delay 411. However, the second delay 512 is selected so that magnetization associated with water is substantially longitudinal and magnetization associated with fat is substantially transverse after the pulse segment 405. Because of the delay difference $\delta\tau = \frac{1}{4}\Delta f$, the water and fat magnetizations are approximately orthogonal at the end of the second interval 512 so that the AHP pulse segment can rotate the water magnetization to be longitudinal while leaving the fat magnetization in the transverse plane. The transverse magnetization can be dephased with a spoiling gradient after the pulse segment 405 prior to image acquisition.

FIGS. 6A-7B and 8A-9B illustrate estimated normalized magnetizations $M_z/M_{equ}$ as a function of $B_0$-based offset frequency and $B_1$ magnitude for equal intervals and unequal intervals, respectively, at various times during the application of the pulse sequence. These estimates were obtained by solving the Bloch equation as a function of time with a tan/tan h modulation function with a 1.25 ms AHP pulse duration, a delay $\tau = 5$ ms, a delay difference of $\delta\tau = 560$ μs and ignoring relaxation terms. As shown in FIG. 6F, the normalized magnetization is near 1 for a broad range of resonance frequencies and $B_1$ magnitudes greater than about 0.20 Gauss. As shown in FIG. 8F, the normalized magnetization is substantially 1 for frequencies within about 200 Hz of the water characteristic frequency for $B_1$ magnitudes greater than about 0.20 Gauss. Thus, the additional delay $\delta\tau$ permits substantial reduction of signals associated with the fat component that is frequency shifted from the frequency associated with water spins.

Representative Phantom and In-Vivo Images

Both phantom and in vivo images have been acquired using the pulse sequences described above. The $T_2$ prep amplitude and phase modulation functions were calculated real-time in an imaging system during pulse sequence application. The $T_2$ prep sequence is followed by a 2D gradient echo imaging sequence. Representative examples were obtained using a GE Signa Excite 3.0T MR imaging system having a maximum gradient amplitude of 4 G/cm, a maximum gradient slew rate of 150 G/cm/ms and using a body coil for signal transmission and detection. Image analyses were performed off-line using image processing methods implemented in MATLAB numerical analysis software.

Figure 12:
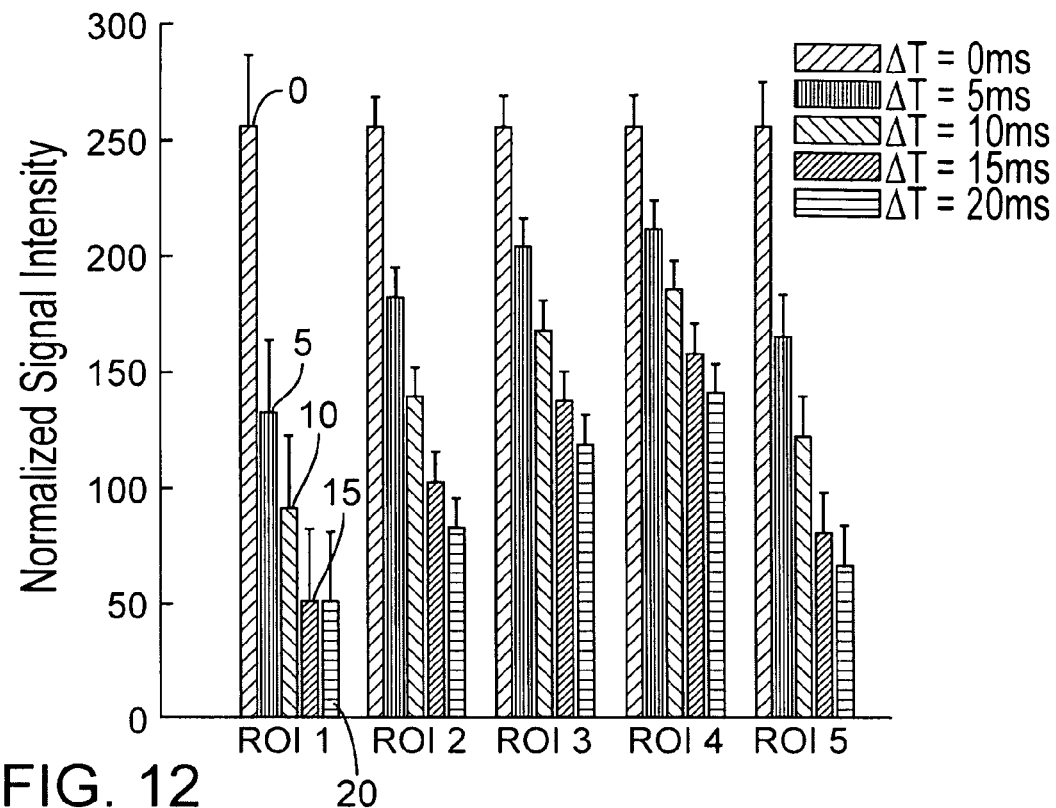
FIG. 12 is a graph comparing signal intensities (in arbitrary units) from the different $T_2$ regions of interest (ROIs) in the images of FIGS. 10A-10E as a function of delay.

A first set of phantom images is shown in FIGS. 10A-10E. Five different tubes were filed with fluids with various values of $T_1$ and $T_2$. The $T_2$ preparation sequence was followed by a gradient recalled echo imaging acquisition sequence with the following imaging parameters: TR=20 ms, TE=6.6 ms, FOV=38 by 38 cm², BW=15.6 kHz with acquisition matrix of 256 by 128. In order to let the magnetization fully recover, a wait time of 500 ms. was inserted after each phase encoding step. Images were obtained with delays $\tau$ of 0, 5, 10, 15, and 20 ms (FIGS. 10A-10E, respectively) without the extra fat saturation delay. The images demonstrate contrast changes achieved by increasing the delay time $\tau$. Normalized signal intensity for the various delays are shown in FIG. 12.

Figures 11A, 11B:
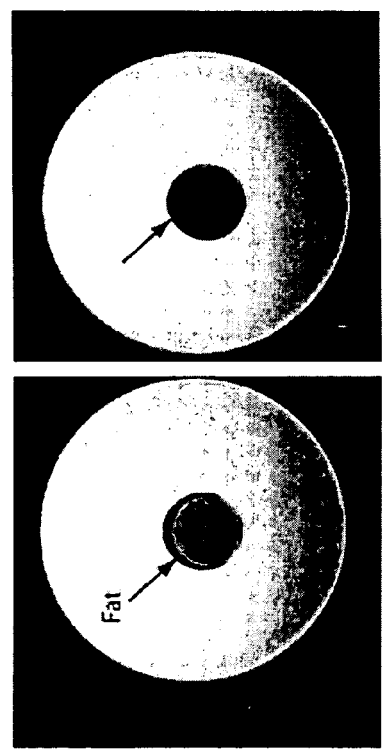
FIGS. 11A-11B are representative images of a phantom containing a fat region obtained with an adiabatic $T_2$-prep sequence without fat saturation and with fat saturation, respectively.

Images demonstrating fat saturation and $T_2$ prep are shown in FIGS. 11A-11B. A doped water phantom having a central fat-containing tube was imaged. Images were acquired without and with additional delay $\delta\tau = 560$ μs (FIGS. 11A-11B, respectively). Imaging parameters were as follows: TR=20 ms, TE=6.7 ms, FOV=30 by 30 cm², BW=15.6 kHz, and acquisition matrix of 256 by 128. The reduced contribution of the fat signal is apparent in FIG. 11B.

Figure 14A:
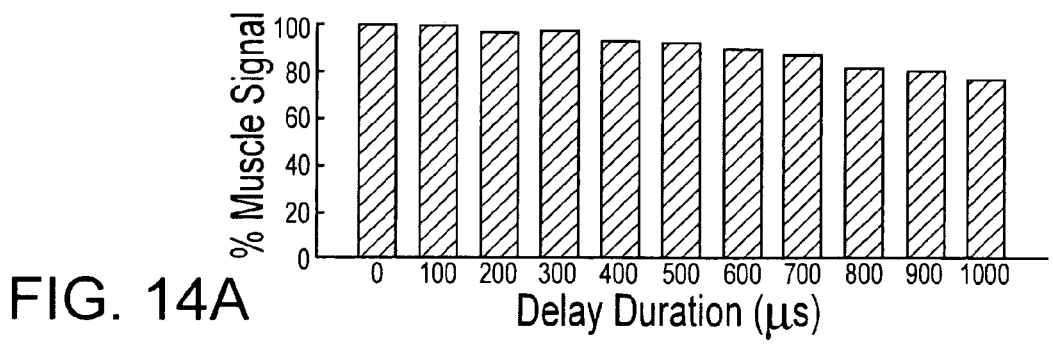
FIGS. 14A-14B illustrates normalized muscle and fat signal magnitudes, respectively, for a region of interest in a thigh obtained by changing the additional fat sat delay of $\delta\tau$ from 0 ms to 1 ms. The decrease in the fat associated signal at a delay of about 600 µs is apparent in FIG. 14B.
Figure 14B:
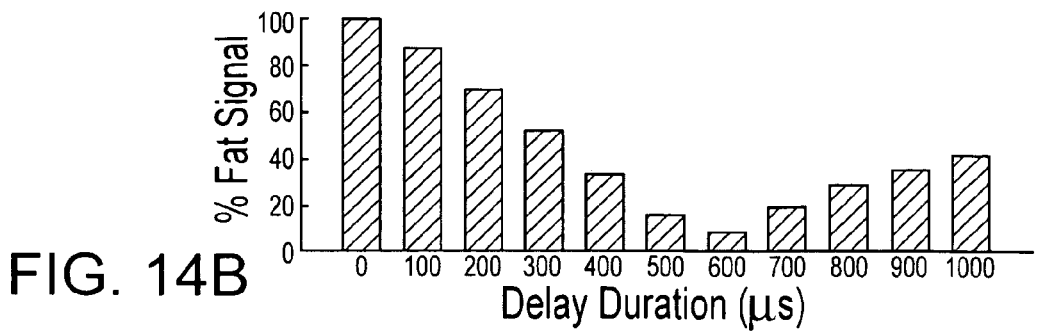
Figure 15:
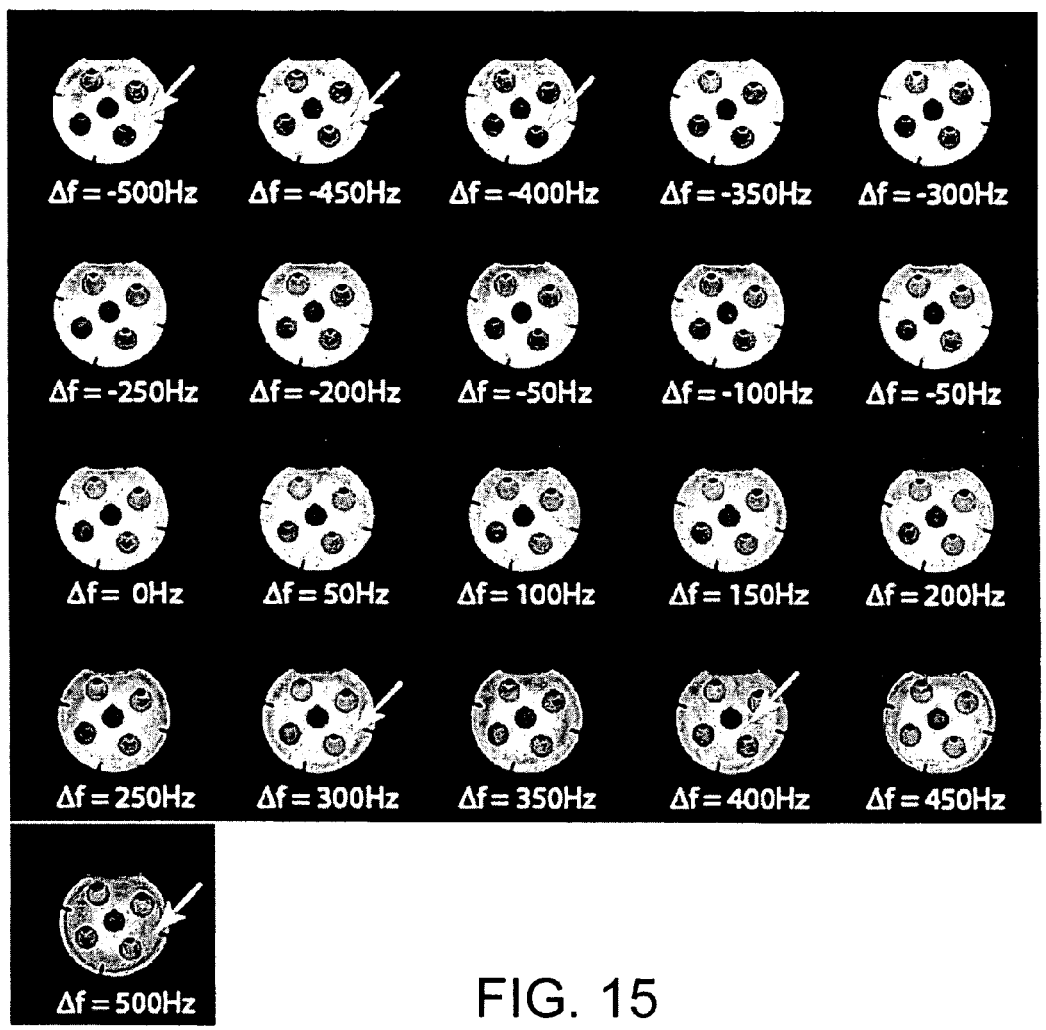
FIG. 15 contains examples of phantom images acquired using $B_1$ insensitive $T_2$ prep with a symmetric insertion delay $\tau$=10 ms in presence of $B_0$ field inhomogeneity. The center frequency was varied in steps of 50 Hz from −500 Hz to 500 Hz to demonstrate the robustness of this $T_2$ prep sequence to field changes.
Figure 16:
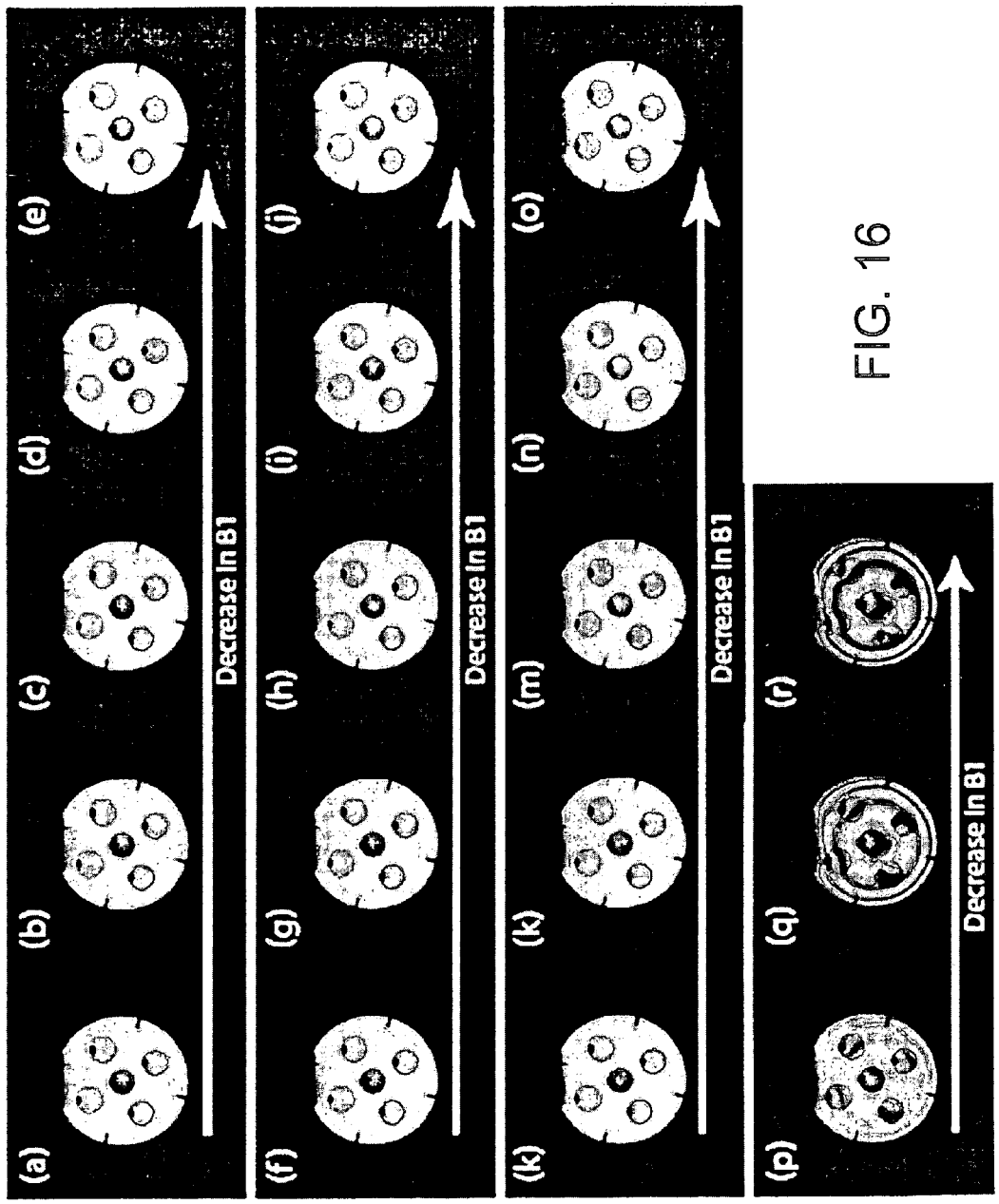
FIG. 16 contains examples of phantom images acquired using $B_1$ insensitive $T_2$ prep with a symmetric insertion delay $\tau$=10 ms in presence of $B_1$ field inhomogeneity. Transmitted $B_1$ field was reduced from (a) to (r) to demonstrate robustness to changes in $B_1$ magnitude. The images show significant artifacts when the amplitude of $B_1$ does not satisfy the adiabaticity condition.

Axial images of a calf and a thigh were obtained to demonstrate the clinical effectiveness of $T_2$ prep sequences as described above. $T_2$ prep is followed by a gradient echo image acquisition sequence with the following imaging parameters: TR=20 ms, TE=6.6 ms, FOV=38 by 38 cm$^2$, BW=15.6 kHz with an acquisition matrix of 256 by 128 elements. In order to let the magnetization fully recover, a wait time of 500 ms is inserted after each phase encoding step. Images were obtained by changing the insertion delay from 0 to 20 ms in 5 ms steps with (FIGS. 13F-13J) and without (FIGS. 13A-13E) the extra fat saturation delay to demonstrate contrast changes achieved by increasing the delay time and saturation of the fat signal. Image regions corresponding to fat are noted with arrows in FIGS. 13A-13E, and suppression of the fat signal associated with these regions is apparent in FIGS. 13F-13J. FIGS. 14A-14B illustrate normalized water and fat signals as a function of extra delay δτ. Delays of about 500-600 µs tend to reduce fat signal substantially.

Spectrally selective magnetic field insensitive $T_2$ prep imaging methods and apparatus are described above. In contrast to conventional techniques that are strongly dependent of the magnitude of $B_1$, the disclosed methods are substantially independent of field magnitude so long as adiabatic pulse conditions are established.

Some principles of the disclosed technology are described with reference to particular adiabatic pulse waveforms, but other adiabatic, quasi-adiabatic, partially adiabatic and/or pseudo-adiabatic pulses can be used. Typically, adiabatic pulses such as adiabatic full passage pulses and adiabatic half passage pulses produce magnetization rotations of about 180° and 90°, respectively, for a range of $B_1$ field strengths, and thus produce rotations that are substantially independent of $B_1$ field strength. Such adiabatic pulses have sufficient bandwidth to refocus substantially all spins in a sample. Other pulses and pulse sequences such as partially adiabatic pulses as described in, for example, Tesiram and Bendall, "Universal Equations for Linear Adiabatic Pulses and Characterization of Partial Adiabaticity," J. Magn. Res. 156:26-40 (2002) or pseudo-adiabatic pulses as described in, for example, Beaudoin and Côté, "The pseudo-adiabatic RF pulse: a fast adiabatic quality RF pulse with low SAR," Proc. Intl. Soc. Mag. Reson. Med. 10 (2002) and Barker et al., "Broadband Proton Decoupling for In Vivo Brain Spectroscopy in Humans," Mag. Reson. Med. 45:226-232(2001). Pseudo-adiabatic pulses are generally based on a sequence of RF pulses applied along a respective series of axes. For example, a series of 1, . . . , Np pulses applied in a yz plane at angles of 90/(Np+1), . . . , 90Np/(Np+1) with respect to the z-axis can effectively rotate a longitudinal magnetization (a z-directed magnetization) into the transverse plane. A set of such sequentialized RF pulses can be referred to generally as a pseudo-adiabatic pulse or pseudo-adiabatic pulse sequence.

As described herein a $B_1$ insensitive magnetization preparation scheme is disclosed that can combine $T_2$ preparation and fat suppression. In other examples, water signal can be suppressed and fat enhanced, or different sample constituents can be enhanced or suppressed by selecting an appropriate delay interval based on a difference Larmor frequencies. The examples are described for operation at 3 T, but can be used at lower or higher field strengths. Delays can be adjusted based on the dependence of Larmor frequency on magnetic field strength. For example, a 440 Hz difference frequency at 3 T corresponds to a 220 Hz difference frequency at 1.5 T. Different pulse modulations can be used, and insensitivity to B1 field variations can depend on a selected pulse modulation. The disclosed examples are representative examples only, and it will be apparent that these disclosed embodiments can be modified in arrangement and detail without departing from the scope of the disclosure. We claim all that is encompassed by the appended claims.

We claim:

1. A magnetic resonance imaging method, comprising:
    situating a sample in a longitudinal magnetic field to establish a longitudinal specimen magnetization;
    applying a reverse adiabatic half passage pulse so as to produce a substantially transverse magnetization from the longitudinal magnetization;
    allowing the transverse magnetization to evolve for a first time interval;
    applying a matched adiabatic full passage pulse so as to substantially invert the transverse magnetization;
    allowing the transverse magnetization to evolve for a second time interval; and
    applying a matched adiabatic half passage pulse so as to produce a $T_2$-weighted longitudinal magnetization from the evolved transverse magnetization.

2. The method of claim 1, further comprising obtaining a $T_2$-weighted image based on the $T_2$-weighted longitudinal magnetization.

3. The method of claim 1, wherein a first portion of the matched adiabatic full passage pulse corresponds to the matched adiabatic half passage pulse, and a second portion of the matched adiabatic full passage pulse corresponds to the matched reversed adiabatic half passage pulse.

4. The method of claim 1, wherein the first time interval and the second time interval are substantially the same.

5. The method of claim 1, wherein the specimen includes spins of a first constituent and spins of a second constituent, and a difference between the first time interval and the second time interval is selected so that the matched adiabatic half passage pulse produces a longitudinal magnetization associated with primarily the first constituent.

6. The method of claim 5, wherein the adiabatic half passage pulse produces a transverse magnetization associated with primarily the second constituent, and further comprising applying at least one gradient field so as to reduce signal contributions from the second constituent.

7. The method of claim 5, wherein the difference between the first time interval and the second time interval is selected based on a difference between Larmor frequencies of the spins of the first constituent and the spins of a second constituent.

8. The method of claim 7, wherein the first constituent is water and the second constituent is fat.

9. A computer readable medium, containing computer-executable instructions for performing, on a sample situated in a longitudinal magnetic field such that a longitudinal specimen magnetization is established, the method comprising:
    applying a reverse adiabatic half passage pulse so as to produce a substantially transverse magnetization from the longitudinal magnetization;
    allowing the transverse magnetization to evolve for a first time interval;
    applying a matched adiabatic full passage pulse so as to substantially invert the transverse magnetization;
    allowing the transverse magnetization to evolve for a second time interval; and applying a matched adiabatic half passage pulse so as to produce a $T_2$-weighted longitudinal magnetization from the evolved transverse magnetization.

10. A method, comprising:
applying a series of pulse sequences comprising a reverse adiabatic half passage pulse, an adiabatic full passage pulse, and an adiabatic half passage pulse, wherein the pulses are matched;
selecting durations of a first time interval and a second time interval, wherein the adiabatic full passage pulse is applied after the first interval elapses after the reverse half passage pulse is applied and the adiabatic half passage pulse is applied after the second time interval elapses after the adiabatic full passage pulse is applied;
obtaining specimen images for a plurality of durations of the first interval and the second interval; and
identifying at least two sample constituents based on the images.

11. The method of claim 10, wherein the constituents are water and fat.

12. A computer readable medium, containing computer executable instructions for the method comprising:
applying a series of pulse sequences comprising a reverse adiabatic half passage pulse, an adiabatic full passage pulse, and an adiabatic half passage pulse, wherein the pulses are matched;
selecting durations of a first time interval and a second time interval, wherein the adiabatic full passage pulse is applied after the first interval elapses after the reverse half passage pulse is applied and the adiabatic half passage pulse is applied after the second time interval elapses after the adiabatic full passage pulse is applied;
obtaining specimen images for a plurality of durations of the first interval and the second interval; and
identifying at least two sample constituents based on the images.

13. A method, comprising:
applying a first adiabatic half passage pulse to specimen to produce a substantial transverse magnetization;
allowing a time interval to elapse;
applying a matched adiabatic full passage pulse during the first time interval,
applying a matched second adiabatic half passage pulse to the specimen after the time interval to rotate at least a portion of the transverse magnetization into a longitudinal magnetization; and
obtaining an image based on the longitudinal magnetization.

14. The method of claim 13, wherein the transverse magnetization includes portions associated with a first sample constituent and a second sample constituent, and the adiabatic full passage pulse is applied at a time point in the time interval so that only the magnetization portion associated with one of the sample constituents is substantially rotated by the second adiabatic half passage pulse so as to become a longitudinal magnetization.

15. The method of claim 14, wherein the transverse magnetization includes portions associated with a first sample constituent and a second sample constituent, and further comprising dividing the time interval into a first subinterval and a second subinterval, wherein a difference between the first subinterval and the second subinterval is based on a difference between a Larmor frequency of the first sample constituent and a Larmor frequency of the second sample constituent.

16. A method, comprising;
determining a frequency shift associated with spins of first and second sample constituents in a longitudinal magnetic field;
producing a first transverse magnetization associated with the spins of the first sample constituent and a second transverse magnetization associated with the spins of the second sample constituent;
selecting a time interval based on the frequency shift so that the first and second transverse magnetizations are substantially orthogonal; and
rotating only the first transverse magnetization with an adiabatic pulse so as to be a longitudinal magnetization; and
obtaining an image based on the rotated magnetization.

17. The method of claim 16, further comprising applying a gradient to spoil the second transverse magnetization.

18. The method of claim 16, wherein the first and second sample constituents are fat and water, respectively.

19. The method of claim 16, wherein the image is based on a transverse relaxation time of the first sample constituent.

20. The method of claim 16, further comprising alternately selecting the first and second transverse magnetizations to be the longitudinal magnetization.

21. A magnetic resonance imaging apparatus, comprising:
an adiabatic pulse generator configured to produce a pulse sequence that includes a reverse adiabatic half passage pulse, a matched adiabatic full passage pulse, and a matched adiabatic half passage pulse; and
a pulse controller configured to direct the adiabatic pulse generator to produce the matched adiabatic full passage pulse at a first time after the reverse adiabatic half passage pulse and to direct the pulse controller to produce the matched adiabatic half passage pulse at a second time after the matched adiabatic full passage pulse.

22. The apparatus of claim 21, wherein the pulse controller determines at least one of the first time and the second time based on a frequency associated with Larmor frequencies of at least a first specimen constituent and a second specimen constituent.

23. The apparatus of claim 22, wherein the first specimen constituent and the second specimen constituent are water and fat, respectively.

* * * * *